United States Patent
Peled et al.

(10) Patent No.: US 9,316,592 B2
(45) Date of Patent: *Apr. 19, 2016

(54) LIGHT-EMITTING INTRA-CAVITY INTERFEROMETRIC SENSORS

(75) Inventors: Asher Peled, Even Yehuda (IL); Menachem Nathan, Tel Aviv (IL); Shlomo Ruschin, Herzlia (IL); Yifaat Betzalel, Givataim (IL); Judith Rishpon, Rehovot (IL)

(73) Assignee: Tel Aviv University Future Technology Development Ltd., Tel Aviv (IL)

( * ) Notice: Subject to any disclaimer, the term of this patent is extended or adjusted under 35 U.S.C. 154(b) by 987 days.

This patent is subject to a terminal disclaimer.

(21) Appl. No.: 13/487,205

(22) Filed: Jun. 3, 2012

(65) Prior Publication Data

US 2012/0244633 A1    Sep. 27, 2012

Related U.S. Application Data

(63) Continuation of application No. 12/402,539, filed on Mar. 12, 2009, now Pat. No. 8,218,151.

(51) Int. Cl.
*G01N 33/551* (2006.01)
*G01N 21/77* (2006.01)

(52) U.S. Cl.
CPC .... *G01N 21/7703* (2013.01); *G01N 2021/7779* (2013.01)

(58) Field of Classification Search
None
See application file for complete search history.

(56) References Cited

U.S. PATENT DOCUMENTS

| | | | |
|---|---|---|---|
| 5,081,012 A | 1/1992 | Flanagan et al. |
| 5,173,747 A | 12/1992 | Boiarski et al. |
| 5,442,169 A | 8/1995 | Kunz |
| 5,465,151 A | 11/1995 | Wybourne et al. |
| 5,591,407 A | 1/1997 | Groger et al. |

(Continued)

FOREIGN PATENT DOCUMENTS

| | | |
|---|---|---|
| EP | WO9937996 | 7/1999 |
| EP | 1058358 | 12/2000 |

(Continued)

OTHER PUBLICATIONS

Selvarajan A et al: "Optical Amplification and Photosensitivity in Sol-Gel Based Waveguides" IEEE Journal of Quantum Electronics, IEEE Service Center, Piscataway, NJ, USA, LNKD-DOI: 10.1109/3.945316, vol. 37, No. 9, Sep. 1, 2001, pp. 1117-1126.

(Continued)

*Primary Examiner* — Chris L Chin
(74) *Attorney, Agent, or Firm* — Mark M. Friedman (57) ABSTRACT

Light-emitting intra-cavity interferometric (ICI) optical sensors based on channel waveguide structures which include an internal light emitting material and a functionalized region. In some embodiments, the waveguides are made of a sol-gel which incorporates the light emitting material. In some embodiments, the waveguide structure includes an ICI resonator backbone and the ICI sensor is a laser sensor. In some embodiments, the resonator backbone has an interferometric Y-branch shape. In some embodiments, the resonator backbone has a Mach Zehnder interferometer shape. In some embodiments, an ICI laser sensor has an interferometric arrayed waveguide grating shape. In some embodiments, an ICI sensor may be remotely optically pumped and remotely read.

24 Claims, 10 Drawing Sheets

(56) References Cited

U.S. PATENT DOCUMENTS

| | | | |
|---|---|---|---|
| 5,623,561 A | 4/1997 | Hartman | |
| 5,655,041 A * | 8/1997 | Forrest | G02B 6/4225 |
| | | | 372/50.1 |
| 6,137,576 A * | 10/2000 | Pauluth | G01N 21/45 |
| | | | 356/477 |
| 6,429,023 B1 | 8/2002 | Gharavi | |
| 6,493,090 B1 | 12/2002 | Lading et al. | |
| 6,767,515 B2 | 7/2004 | Coldren | |
| 6,899,849 B2 | 5/2005 | Meinhart | |
| 7,061,619 B2 | 6/2006 | Shirai et al. | |
| 7,212,693 B2 | 5/2007 | Carr | |
| 7,447,391 B2 | 11/2008 | Peled | |
| 7,483,140 B1 | 1/2009 | Cho et al. | |
| 7,747,128 B2 | 6/2010 | Kikuchi et al. | |
| 7,957,617 B2 | 6/2011 | Vollmer et al. | |
| 2002/0015155 A1 * | 2/2002 | Pechstedt | G01D 5/266 |
| | | | 356/477 |
| 2004/0081384 A1 | 4/2004 | Datesman et al. | |
| 2004/0120633 A1 * | 6/2004 | Gao | G02B 6/12007 |
| | | | 385/14 |
| 2004/0146849 A1 | 7/2004 | Huang et al. | |
| 2006/0178841 A1 | 8/2006 | Fernandez | |
| 2008/0043248 A1 | 2/2008 | Ozcan | |
| 2009/0097843 A1 * | 4/2009 | McBrien | G02F 1/225 |
| | | | 398/16 |
| 2009/0244542 A1 | 10/2009 | Cho et al. | |
| 2010/0104241 A1 * | 4/2010 | Oikawa | G02B 6/12007 |
| | | | 385/16 |
| 2010/0231920 A1 | 9/2010 | Peled et al. | |
| 2011/0223688 A1 | 9/2011 | Sinclair et al. | |

FOREIGN PATENT DOCUMENTS

| | | |
|---|---|---|
| GB | 2448162 | 10/2008 |
| JP | WO2004034527 | 4/2004 |
| WO | WO0210719 | 2/2002 |

OTHER PUBLICATIONS

Zhanjia Hou et al: "Optical Microdisk fabrication with sol-gel techniques and its application" Proceedings of the SPIE—The International Society for Optical Ebgineering SPIE—Int. Soc. Opt. Eng USA, vol. 4435, 2001, pp. 162-166.

Sanfprd N A et al :"Y-Branch Vvaveguide Glass Laser and Amplifier", Optics Letters, OSA, Optical Society of America, Washington, DC, US, vol. 16, No. 15, Aug. 1, 1991, pp. 1168-1170.

Asher Peled et al :"Neodymiun Doped Sol-Gel Tapered Waveguide Amplilier" Applied Physics Letters, vol. 90, 161125, 2007.

Asher Peled et al :"A Monolithic Rare-Earth Doped Sol-Gel Tapered Rib Waveguide Laser" Applied Physics Letters. vol. 92, 221104, 2008.

T.J. Wang et al."Integrated-Optic Biosensor by Electro-Optically Modulated Surface Plasrnon Resonance" Bioensors and Bioelectronics, vol. 22, pp. 1441-1446, 2007.

* cited by examiner

LIGHT-EMITTING INTRA-CAVITY INTERFEROMETRIC SENSORS

This is a Continuation of pending U.S. patent application Ser. No. 12/402,539, which was filed Mar. 12, 2009.

FIELD OF THE INVENTION

The invention is related to the general field of optical sensors, and more particularly to light emitting intra-cavity interferometric (ICI) channel waveguide (WG) sensors.

BACKGROUND OF THE INVENTION

Optical sensing devices which use various sensing principles are known. A good background description on the state of the art is provided in U.S. Pat. No. 7,447,391 to Asher Peled et al., as well as in "Novel monolithic amplifiers, lasers and intra-cavity interferometric sensors based on Nd-doped sol-gel", PhD thesis, Asher Peled, Tel Aviv University, submitted November 2008, to be published 2009 (hereinafter "Peled 2009"), both of which are incorporated herein by reference in their entirety. In particular, interferometric optical sensors in various configurations, such as Mach Zehnder interferometers (MZI) and Young interferometers are known to have the best reported sensitivities.

U.S. Pat. No. 7,447,391 discloses biological and chemical optical sensing devices comprising at least one planar resonator structure included in a sol-gel light emitting (or simply "emitting") waveguide and at least one biological or chemical probe bound to at least a part of the resonator structure, the probe operative to bind specifically and selectively to a respective target substance, whereby the specific and selective binding results in a parameter change in light emitted from the waveguide. The sensed parameter may be a spectral change, e.g. a spectral shift, or a Q-factor change which is encoded in the emitted optical signal and which may be read remotely by an optical reader. In some embodiments, the resonator structure is linear and the waveguide is "active" or "light-emitting', The "active" or "light-emitting' terminology reflects the incorporation of at least one light emitting material (e.g. photluminescent—"PL" or laser material) in the sol-gel and emission of light generated from this light-emitting material. In some embodiments, this material can be remotely pumped by a remote optical source and excited to emit the light which is outcoupled from the device to a remote detector (e.g. spectrometer).

Amplifiers and lasers based on on Nd-doped sol-gel light-emitting structures are described respectively in A. Peled et al., "Neodimium doped sol-gel tapered waveguide amplifier", Applied. Physics Letters, Vol. 90, 161125, 2007 (hereinafter "Peled 2007") and in A. Peled et al., "A monolithic solid-state laser realized by neodymium doped silica-hafnia sol-gel tapered rib waveguide", Applied Physics Letters Vol. 92, 221104, 2008 (hereinafter "Peled 2008"), both incorporated herein by reference in their entirety.

Light-emitting (for example sol-gel) biosensors such as described above are robust and immune to temporal variations (instabilities) of the optical source power and to the efficiency of light coupling into and out of the sensor chip. This immunity is achieved since these sensors encode the measured parameter in their emission spectrum rather than in the emission intensity. In addition, these sensors can in principle be implantable, because both the pumping and the spectral interrogation of their emitted light are performed remotely. However, their sensitivity is expected to be less than that of interferometric biosensors.

Y-branch waveguide lasers are known, see e.g. N. A. Sanford et al., Optics Letters, Vol. 16, n. 15(1), p. 1168-70, 1991, as well as Peled 2009, page 19 and references therein. The device of Sanford et al. has an "imbalanced" geometry in which the branch segments are mismatched in length by 2.4%. Stanford's device uses external reflectors attached to the structure to achieve resonance and lasing (i.e. his waveguide laser is not monolithic). Prior art Y-branch waveguide lasers are not known to be designed and used for sensing in general and biosensing or chemosensing in particular. When Y-branch waveguide structures were used for biosensing, as in T. J. Wang et al., Biosensors and Bioelectronics, vol. 22, pp. 1441-1446, 2007, they were not lasers but passive devices which do not emit internally generated light.

Immunoassays using optical sensors are normally done in "wet" mode, via a flow cell in which a sample liquid flows on the sensor surface. This enables to measure the chemical kinetics of interactions and to evaluate kinetic rate constants, as well as to follow interactions during changes introduced to the sample liquid. Nevertheless, wet immunoassays have some serious drawbacks. For example, changes in temperature of the flowing sample liquid strongly impact its refraction index and disrupt the optical reading. The reading is also disturbed by turbulence in the flow. These issues are solved by a sophisticated flow system with a delicate and tight control of the flowing sample liquid temperature. This complexity significantly raises the cost of wet optical immunoassay systems, rendering them inappropriate for point-of-care applications.

There is thus a recognized need for, and it would be advantageous to have, inexpensive and disposable sensors which combine the benefits of the robust spectral interrogation of light-emitting sensors as described above with the sensitivity of interferometric sensors. Moreover, it would be advantageous to use such sensors in dry biological immunoassays (where they serve as biosensors).

SUMMARY OF THE INVENTION

The invention provides, in various embodiments, light-emitting (or simply "emitting") waveguide based optical bio/chemical sensors in intra-cavity interferometric configurations, thereby combining benefits of light-emitting sensors (in spectral interrogation) with the well-known high sensitivity of interferometric devices. Note that a light-emitting sensor in the sense of the invention may be lasers which emit coherent light or devices that emit non-coherent (luminescent) radiation. In some embodiments, the waveguides are implemented in a sol-gel layer. In some embodiments, the sensors have light emitting resonator backbones with an imbalanced Y-branch waveguide structure. In some embodiments, the sensors have light emitting resonator backbones with a Mach-Zehnder intereferometer (MZI) shape. In some embodiments, the sensors have light emitting resonator backbones with an arrayed waveguide grating (AWG) or "phasar" shape. Such sensors are referred to herein as intra-cavity interferometric (ICI) sensors. The resonators (also referred to as cavity resonators or micro-resonators) which shape the emitted radiation spectra are integrated in the waveguides. The light emitting material incorporated in the waveguide structure may be a lasing material, a photo-luminescent material or a chemo-luminescent material.

A sensor of the invention may be used for sensing biological materials, substances or reactions (being therefore a "biosensor") or chemical materials, substances or reactions (being therefore a "chemosensor"). When referring to a target being sensed, "material", "analyte" and "substance" are used interchangeably. A sensor of the invention may also be used to sense temperature, stress or other physical or chemical parameters In contrast with all prior art devices, the emitting ICI sensors of the invention attain the sensitivity of interferometric integrated optical devices while generating internally the emitted sensing signal and encoding it spectrally. They can be used to perform remote or implanted (in-vivo) sensing, since they radiate the sensing signal. Their reading is robust, since their emitted spectrum is insensitive to intensity instabilities arising from instabilities of the pumping light or electrical source or (in optical pumped embodiments) from variations in the light coupling efficiency into and out of the sensor chip. These benefits are combined with the highest sensitivity obtainable in integrated optics devices. These benefits are particularly important in the use of these sensors for diagnostics in point-of-care applications. The sensors can be fully monolithic. In this specification, "monolithic" refers to an integrated structure that includes all the sensor elements (waveguides, resonator elements and in some case light couplers) on a single substrate or "chip", where the pump and the reader (detector/spectrometer) can be external. Moreover, biosensors of the invention can be used in dry immunoassays.

In some embodiments, at least one of the waveguide branches is functionalized (bio-bound or chemo-bound) with probes or "receptors" (e.g. antibodies), while another branch serves as reference. In such embodiments, upon binding of target molecules to the receptors, the propagation coefficient of the guided light (effective index of the WG) is altered at a different rate in the functionalized branch. This leads to a spectral shift of the positive interference pattern of the resonator, which in turn is transformed into a shift of the emitted spectrum of the entire device. Such a structure provides a biological (or chemical) reference which is inherent and integral to the device and which minimizes nonspecific binding effects. In addition, in such a structure, the binding events in the functionalized branch are transformed by interference into a maximal spectral shift, which maximizes the sensitivity. Thus, a mechanism is created to achieve the high sensitivity of interferometric integrated optics devices while the sensing is encoded in the internally generated and out-coupled emitted light spectrum.

In some embodiments, there is provided a sensor including: a Y-branch channel waveguide structure with at least two split waveguide branches; a light emitting material included in the Y-branch channel waveguide structure, wherein light generated in the light emitting material is emitted from the waveguide structure; and a functionalized region on at least one of the split branches, the functionalized region used for binding a target material, the binding detectable by a parameter change in the emitted light. In some embodiments, the sensor further includes input means to in-couple external light used to excite the light emitting material and output means to output the emitted light from the sensor. In some embodiments, the parameter change is a spectral shift. In some embodiments, the sensor is a laser sensor. In some embodiments, an exciting source and/or a reader/detector/spectrometer can be integrated with the waveguide structure and the input and output means on a single sensor chip.

In some embodiments, there is provided a sensor including: a Mach Zehnder interferometer (MZI) channel waveguide structure with at least two MZI branches; a light emitting material included in the waveguide structure, wherein light generated in the light emitting material is emitted from the waveguide structure; and a functionalized region on at least one MZI branch, the functionalized region used for binding a target material, the binding detectable by a parameter change in the emitted light. In some embodiments, the sensor further includes input means to in-couple external light used to excite the light emitting material and output means to output the emitted light from the sensor. In some embodiments, the parameter change is a spectral shift. In some embodiments, the sensor is a laser sensor. In some embodiments, an exciting source and/or a reader/detector/spectrometer can be integrated with the waveguide structure and the input and output means on a single sensor chip.

In some embodiments, there is provided a sensor comprising an intra-cavity interferometric waveguide structure having at least two branches and including a light-emitting material which emits internally generated light, and a functionalized region on at least one branch, the functionalized region used for binding a target material, the binding detectable by a parameter change in the emitted light. In some embodiments, the parameter change is a spectral shift. In some embodiments, the sensor is a laser sensor. In some embodiments, an exciting source and/or a reader/detector/spectrometer can be integrated with the waveguide structure and the input and output means on a single sensor chip.

In some embodiments, there is provided a method for performing an optical immunoassay, comprising the steps of: providing a light-emitting ICI waveguide sensor, functionalizing a waveguide region and performing an immunoassay by measuring a parameter change in the light emitted from the sensor, the parameter change resulting from binding of a target material to the functionalized waveguide region. In some embodiments, the immunoassay is dry.

BRIEF DESCRIPTION OF THE DRAWINGS

The invention is herein described, by way of example only, with reference to the accompanying drawings, wherein.

DETAILED DESCRIPTION OF THE INVENTION

Light-Emitting Intra-Cavity Interferometrie (ICI) Waveguide Sensor

Figure 1:
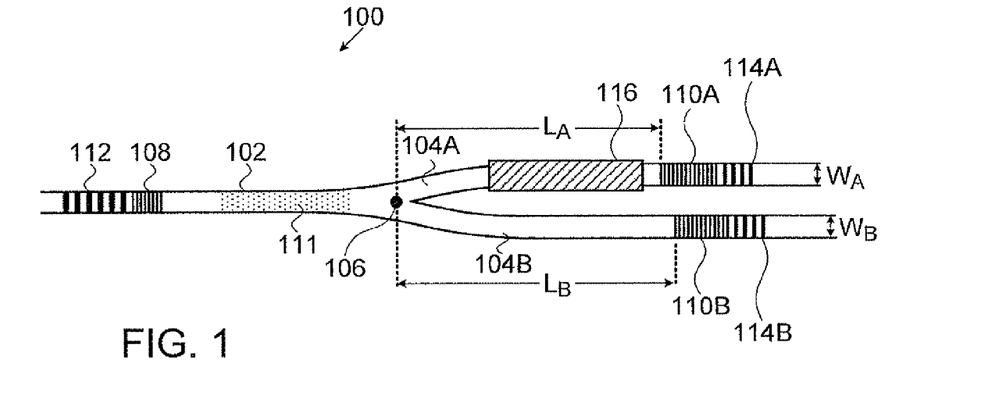
FIG. 1 shows schematically one embodiment of a light-emitting ICI sensor of the invention having an active branch and a reference branch.

FIG. 1 shows schematically an embodiment of a light-emitting ICI waveguide sensor ("device") 100 of the invention. Note that the features shown are not drawn to scale. Device 100 has essentially an imbalanced Y-branch waveguide structure and includes a "common" channel waveguide ("common branch") 102 which splits at a splitting point 106 into two waveguide branches 104a and 104b with respective widths $w_A$ and $w_B$. $w_A$ and $w_B$ may be equal or non-equal. Specifically in FIG. 1, $w_A$ and $w_B$ are shown as equal. In general, a device of the invention may have the common WG split into more than two branches. Specifically, the materials, layer thicknesses and cross sectional structure of a waveguide and the various gratings in the invention may be similar to those of waveguides described in detail in Peled 2007, Peled 2008 and U.S. Pat. No. 7,447,391. In particular, the waveguide material may be a sol-gel. A common branch reflector (in the form of a reflection grating) 108 is located on common WG 102. A branch reflector 110a is located on branch 104a at a distance $L_A$ from splitting point 106 and a branch reflector 110b is located on branch 104b at a distance $L_B$ from splitting point 106. A reflector may be partially or totally reflective. A partially reflective grating enables the transferred light to be coupled out and be measured, as explained in U.S. Pat. No. 7,447,391 and in Peled 2008. A resonator is formed by two reflectors and the waveguide section therebetween, where one of the reflectors is the common branch reflector and the other reflector is a split branch reflector. Thus, a resonator may be defined by pairs of reflectors 108 and 110a and 108 and 110b. $L_A$ and $L_B$ define each a branch length. $L_A$ and $L_B$ may be equal or non-equal. When non-equal, the configuration is essentially that of an imbalanced Y-branch waveguide structure. Specifically in FIG. 1, $L_A$ and $L_B$ are unequal.

A light emitting material 111, for example Neodimium, is incorporated in at least part of a waveguide (here shown in common branch 102). Preferably, the light-emitting material is incorporated in the entire resonator section. The light emitting material may be excited optically or electrically. Some or all of the internally emitted light propagates in both branches and is reflected from their reflectors. Light reflected from the two branches interferes at splitting point 106, introducing a condition additional to the positive interference condition after a roundtrip of a regular (non-split) resonator. This added condition leads to the intra-cavity interferometric effect, which is explained in detail hereinbelow in section "Y-shape ICI laser sensor design and principle of operation" and in its equations (1-5).

In optical pumping embodiments, the pumping light can be coupled from free space to device 100 via an input grating coupler 112, shown here positioned on common branch 102. In some embodiments, the input grating may be positioned on one or both of the Y-branches: Alternatively, the in-coupling may be done by well known in-coupling means such as fiber butt coupling. The internally emitted light may be out-coupled (output) from the device through output grating couplers such as gratings 114a and 114b. Alternatively, the light may be out-coupled through grating coupler 112 which can be designed as a dual purpose grating as described in Peled 2008. In some embodiments, the input and/or output grating may be optional or positioned only on some of the Y-branches. In some embodiments (not shown), the output grating may be positioned on the same branch as the input grating. In some embodiments, the input and output gratings may be designed as a single grating used for both pump input and emitted light output. The internally generated light may also be out-coupled from the device via other out-coupling means to either a fiber, a spectrometer or to free space.

In the embodiment of FIG. 1, a sensing branch (e.g. branch 104a) is functionalized with biological receptors in a functionalized region 116. The other branch (104b) is not functionalized and serves as reference. In another embodiment of a light-emitting ICI sensor 200 shown in FIG. 2, both branches 204a and 204b are functionalized in respective functionalized regions 216a and 216b with same type receptors, with the functionalized regions having different areas (length and/or width). In this case, there is no reference branch. Alternatively, in yet another embodiment of a light-emitting ICI sensor 300 with both branches functionalized, shown in FIG. 3, each branch has a different type of functionalization (e.g. two functionalized regions 316a and 316b with different types of functionalization or different types of receptors). In this case, the functionalization of the reference arm could be designed such as to minimize nonspecific bindings or, for example, an antibody with no activity to the analyte could be used on this arm to provide about the same nonspecific binding rate as in the sensing arm. In yet another embodiment (not shown) neither branch is functionalized, but the branches have different lengths and/or widths. In this case, the sensor may act as a nonspecific chemical sensor (for example to sense nondestructively curing of glue or to read remotely a parameter such as temperature or stress).

Figure 4:
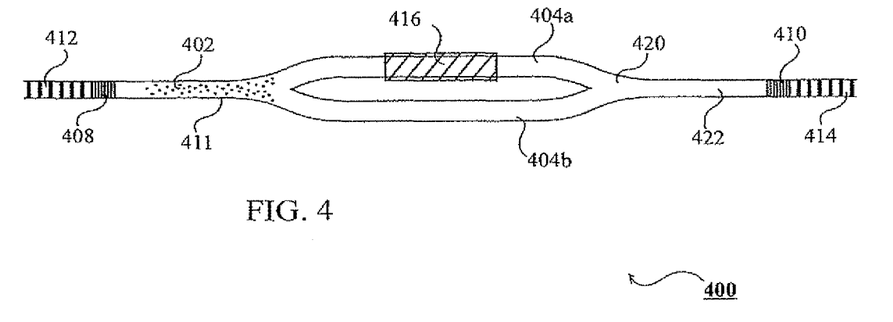
FIG. 4 shows schematically one embodiment of an intra-cavity interferometric light-emitting sensor of the invention having a Mach Zehnder shape for the emitting resonator with a sensing functionalized branch and a reference branch.

In yet another embodiment of a light-emitting sensor 400 shown in FIG. 4, the two split branches of a Y-branch waveguide structure (here 404a and 404b) are further combined at a combining point 420 into a second common branch 422 (FIG. 4) to form an intra-cavity interference in a Mach-Zehnder shape (two Y-branch waveguide structures are essentially joined with their split branches). While MZI devices as well as their use for bio or chemo-sensing are known, there are no known light-emitting ICI sensors in which intra-cavity interference is achieved by a resonator in the shape of a MZI, in which the light emission is internal and in which the internally emitted light may be shaped (e.g. into a free-space laser beam). In order to have such a light-emitting MZI sensor, the device must include cavity resonators which supply feedback and support resonance and an active medium (light-emitting material) 411 able to generate the light. In one embodiment, such a resonator is formed by a reflector 408 located on a first common branch 402 and by a reflector 410 located on common branch 422. Device 400 is also shown to include an input grating coupler 412, a functionalized region 416 on branch 404a and an output grating coupler 414. As in the other ICI sensors described above, in some embodiments, these gratings are optional and may not be needed. In some embodiments (not shown), an output grating may be positioned on the same branch as the input grating. In some embodiments (not shown), the input and output gratings may be designed as a single grating used for both pump input and emitted light output ("dual use").

Figure 2:
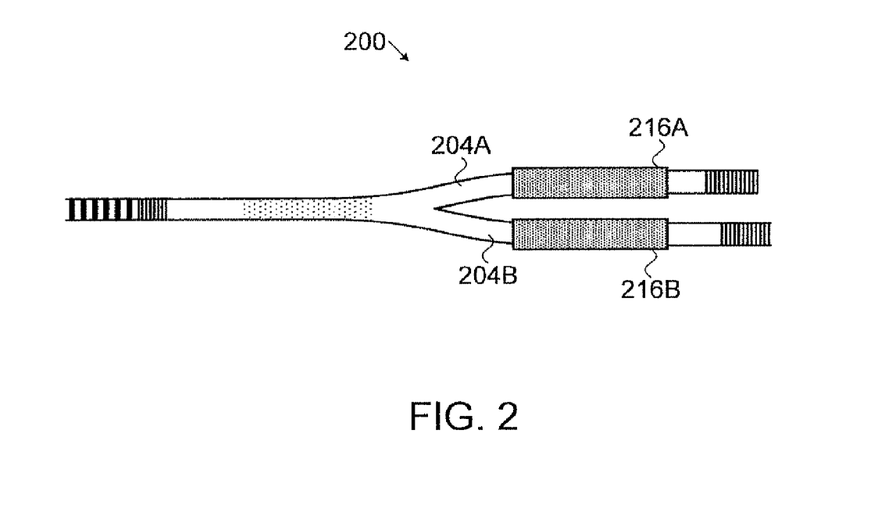
FIG. 2 shows schematically a device as in FIG. 1 having two branches with the same type of functionalization (bio-binding or chemo-binding) on each branch but with different functionalized regions.
Figure 3:
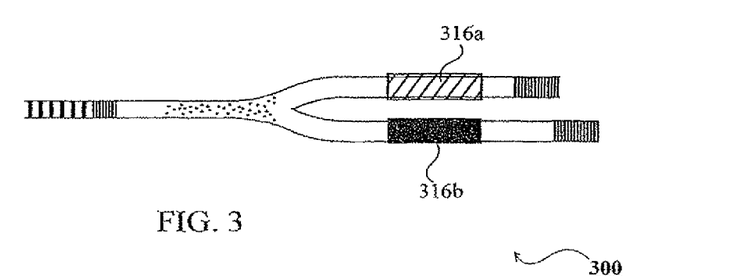
FIG. 3 shows schematically a device as in FIG. 1 having two branches with a different type of functionalization on each branch.

The light-emitting MZI sensors may be functionalized as in any of the schemes shown in FIGS. 1-3: as in FIG. 1, with one functionalized branch and one reference branch; as in FIG. 2, with two same type functionalized branches but different functionalized region sizes (different length and/or width); or as in FIG. 3, with different type functionalizations on each branch, regardless of the functionalized region size.

In contrast with prior art interferometric sensors, the readout of a light-emitting interferometric sensor of the invention is the spectral alteration of the light generated internally and emitted from the device. The spectral alteration is in response to binding events on functionalized branches vs. non-functionalized branches, to binding events with different rates on different-type functionalized branches with same or different functionalization regions or to binding events on same-type functionalized branches with different functionalization regions.

In each of the aforementioned MZI embodiments, each of the reflectors may be fully reflective or partially transmitting. The internally generated light may be out-coupled from the device to free space via a grating coupler, via the input grating coupler for the pump, which in this case is designed for dual use, or via other out-coupling means. Alternatively, the emitted light may be detected or analyzed on the chip by an integrated spectrometer (not shown).

Figure 5:
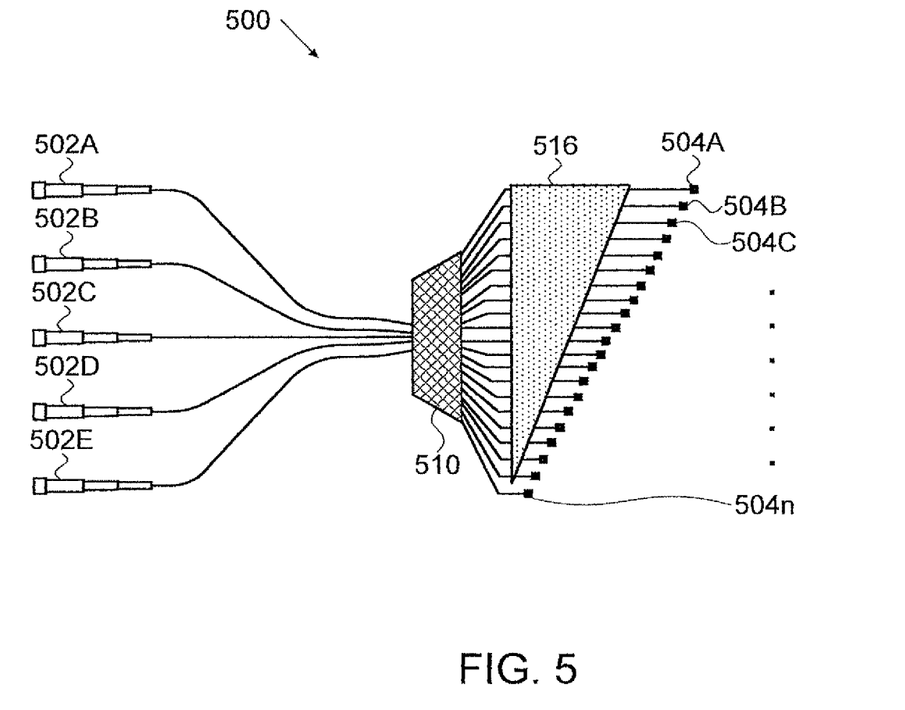
FIG. 5 shows schematically one embodiment of a light-emitting ICI sensor of the invention in the shape of an arrayed waveguide grating or phasar.
Figure 6:
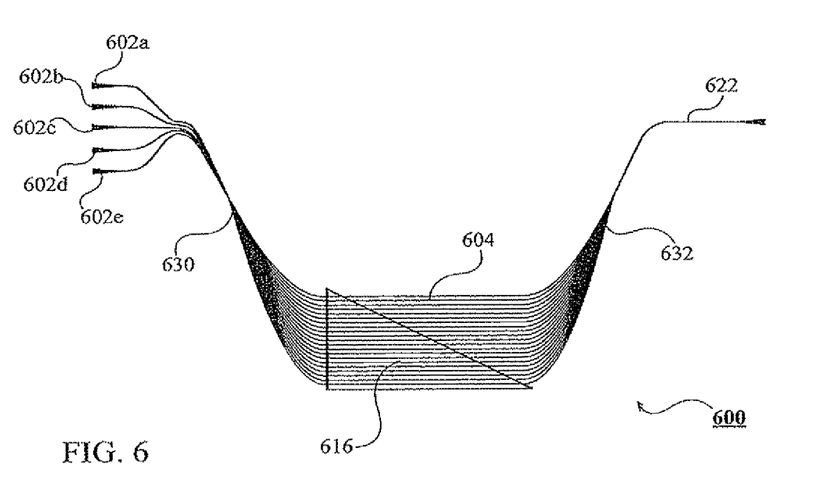
FIG. 6 shows schematically another embodiment of a light-emitting ICI sensor of the invention in the shape of an arrayed waveguide grating or phasar.

In some embodiments, light-emitting Y-shaped or MZI shaped ICI sensors of the invention may have more than two branches, as shown respectively in embodiments 500 in FIG. 5, and 600 in FIG. 6. The extension of the device design and of the functionalization schemes from two branches to more than two branches should be clear to one of ordinary skill in the art. In particular, embodiment 500 includes light-emitting waveguide sensors of the invention having five common WGs (branches) 502a-f combine and split at a combiner/splitter 510 (as in well known waveguide array configurations and phasars). Split-branches 504 are provided at the exit of combiner/splitter 510. With such a structure for the ICI resonator backbone, one may gain sharper peaks in the emission spectra, an enhanced FSR and enriched degrees of freedom in the design, which can be used to improve sensitivity. Each common WG and each branch has a reflector (not shown because of the scale). Therefore, resonators may be formed between the reflector on the common arm and that on any branch. A triangular shaped area marked 516 indicates different functionalization lengths of different branches functionalized with the same or different receptors. Embodiment 500 allows therefore implementation of different resonator geometries and further enhances the sensor sensitivity as well as its versatility.

The same idea is extended to Arrayed Waveguide Grating (AWG) or phasar type geometries shown in FIG. 6. Here, each of five common WGs 602a-e may be split at a splitter 630 into at least two branches. All branches 604 are recombined into a single common branch 622 by a combiner 632. A general area of functionalized branches is shown as a triangle 616. As with embodiment 500, the triangular shape indicates different lengths of different branches which are functionalized with the same or different receptors. Any combination of functionalization areas and types described above with reference to two-branch sensors is applicable here as well, as would be clear to one with ordinary skill in the art. Each common WG has a reflector (not shown because of the scale). Therefore, resonators are formed between the common branch reflectors through each split branch. As with the structure in embodiment 500, here too one may gain sharper peaks in the emission spectra, an enhanced FSR and enriched degrees of freedom in the design, which can be used to improve sensitivity.

Y-Shape ICI Laser Sensor Design and Principle of Operation

In an embodiment, the common waveguide (branch) dimensions and cross-section are identical to those of the channel waveguide laser described in detail in Peled 2008, including the same 7 mm long tapering section with a similar input/output grating coupler. In a Y-branch waveguide resonator of the invention, the common branch then splits at the narrow (for example 4 μm) section into two single mode waveguides (e.g. 104a and 104b in FIG. 1). As mentioned, in some embodiments, only one branch is functionalized with receptors, while the other branch serves as reference. This architecture maximizes the sensor's response (expressed for example by a spectral shift) due to binding of the target material to the immobilized receptors (equations 1 to 5 below), and also supplies an inherent and integral reference, within the device, which minimizes the sensor response to nonspecific bindings (which may occur on both branches). In such a configuration, the two guided waves reflected from the total reflectors at each end of the waveguide branches (110a and 110b) interfere at the Y junction. Their interference introduces an additional condition for lasing (or, in the PL case, oscillation and emission), which is added to the regular condition of repetitive phase after a full round trip in the resonator. In an exemplary 3 cm long resonator, the Free Spectral Range (FSR) of the longitudinal modes is of the order of 0.01 nm. As a consequence of sensitivity considerations (see below the paragraph after equation 5 and Peled 2009, pages 48-50), the positive interference bandwidth is of the order of 2 nm. Therefore, the conditions for positive interference of the two branch waves determine a spectral envelope in which the longitudinal modes and hence the lasing wavelengths are densely populated. The conditions for positive interference of the two branches are given next, in order to follow the lasing spectral shift as a response to the analyte (bio-target material) binding.

The condition for phase match of the two waveguide branch waves is:

$$2\left(\frac{2\pi n_{eff_B}}{\lambda}L_B - \frac{2\pi n_{eff_A}}{\lambda}L_A\right) = 2\pi N \quad (1)$$

where $n_{eff_A}$ and $n_{eff_B}$ are the effective indices of the functionalized (sensing) branch and of the reference branch, respectively, and $L_A$, $L_B$ are their lengths. $\lambda$ is the optical wavelength in vacuum and N is an integer. The propagation constant (effective index) of a channel waveguide may be calculated by well known methods, see for example Chiang, K. S., Applied Optics, v 25, n 13, p 2169-74, (1986) and Kim, C. M., Jung, B. G., Lee, C. W., Electronics Letters, v 22, n 6, March 13, p 296-298, (1986). The impact of added bio-layers on the propagation constant of a functionalized waveguide section may be evaluated by calculating an impact of such layers on a slab waveguide with the same layer thicknesses. Calculation details are given in Peled 2009. Note that for MZI shape ICI laser sensor designs, the factor 2 in the left side of Equation 1 is dropped and $L_A$, $L_B$ stand for the branch lengths from the split junction to the combining junction.

The optical wavelengths in which the positive interference occurs are:

$$\lambda_{peak} = 2\frac{n_{eff_B}L_B - n_{eff_A}L_A}{N} \quad (2)$$

If $\lambda_{peak_0}$ designates the designed peak wavelength according to which the waveguide branch difference is chosen, then the interference order N may be directly expressed as:

$$N = 2\frac{n_{eff_B} L_B - n_{eff_A} L_A}{\lambda_{peak_0}} \qquad (3)$$

$n_{eff_{Ab}}$ designates the effective index of the functionalized branch after binding the analyte. The positive interference peak wavelength after this binding $\lambda_{peak_b}$ would then be:

$$\lambda_{peak_b} = \frac{n_{eff_B} L_B - n_{eff_{A_b}} L_A}{n_{eff_B} L_B - n_{eff_A} L_A} \lambda_{peak_0} \qquad (4)$$

The corresponding peak wavelength shift $\Delta_b \dot\lambda_{peak}$ with respect to the change of the effective index due to bio-layer binding is:

$$\Delta_b \lambda_{peak} = \frac{d\lambda_{peak}}{dn_{eff_{A_b}}}\left(n_{eff_{A_b}} - n_{eff_A}\right) = \frac{L_A \lambda_{peak_0}}{n_{eff_A} L_A - n_{eff_B} L_B}\left(n_{eff_{A_b}} - n_{eff_A}\right) \qquad (5)$$

The peak wavelength shift as a response to analyte binding $\Delta_b \lambda_{peak}$ can be enlarged by either elongating $L_A$ or by reducing the factor ($n_{eff_A} L_A - n_{eff_B} L_B$), which is the initial optical path difference between the sensing branch and the reference branch.

Another design consideration is that at any spectral shift, there would still be at least one positive interference peak that enables the lasing action. Hence, in exemplary embodiments, the initial branch optical path difference was designed to be 60 μm in order to shape an interference pattern with a FSR of about 5 nm. Such a spectral spacing guaranties that, at any spectral shift, there is at least one positive interference peak for which the power reflection coefficient of 210 nm deep reflection gratings (used exemplarily in the experimental devices, of which results are presented hereafter) does not fall by more than a few percent from its maximum value. Under these conditions, the positive interference peak bandwidth is of the order of 2 nm.

Example

C Reactive Protein (CRP) (152315, MP) was chosen as a model for an analyte. CRP is a pentameric plasma protein, which its blood levels indicate risk of cardio vascular seizures. Hence, there is a need for a simple, cheap and rapid way to measure its concentration in blood. BSA (Bovine serum albumin, A7906, Sigma) served as a control protein.

Sol-gel ICI laser sensors with three exemplary sets of imbalanced branch lengths $L_A$ and $L_B$ were designed and fabricated in a sol-gel layer on top of a silica-on-silicon substrate. Details of the sol-gel waveguide fabrication may be found in Asher Peled et al., "Amplification from $Nd^{+3}$ doped Si—Ti sol-gel channel waveguides", J. Optical Materials, 2009, in press, and in Peled 2009. Each design was fabricated in a number of copies. Sensor type #1, where $L_A$ and $L_B$ were respectively 3 mm and 3.06 mm; Sensor type #2, where $L_A$ and $L_B$ were respectively 10 mm and 10.06 mm; and Sensor type #3, where $L_A$ and $L_B$ were respectively 20 mm and 20.06 mm. All devices had a total length of 30 mm and the common branch had a 7 mm tapering section as in the linear lasers described in Peled 2008. All sensors were bio-functionalized as described next with reference to FIGS. 7-9.

Exemplary Bio-Functionalization Scheme

Figure 7:
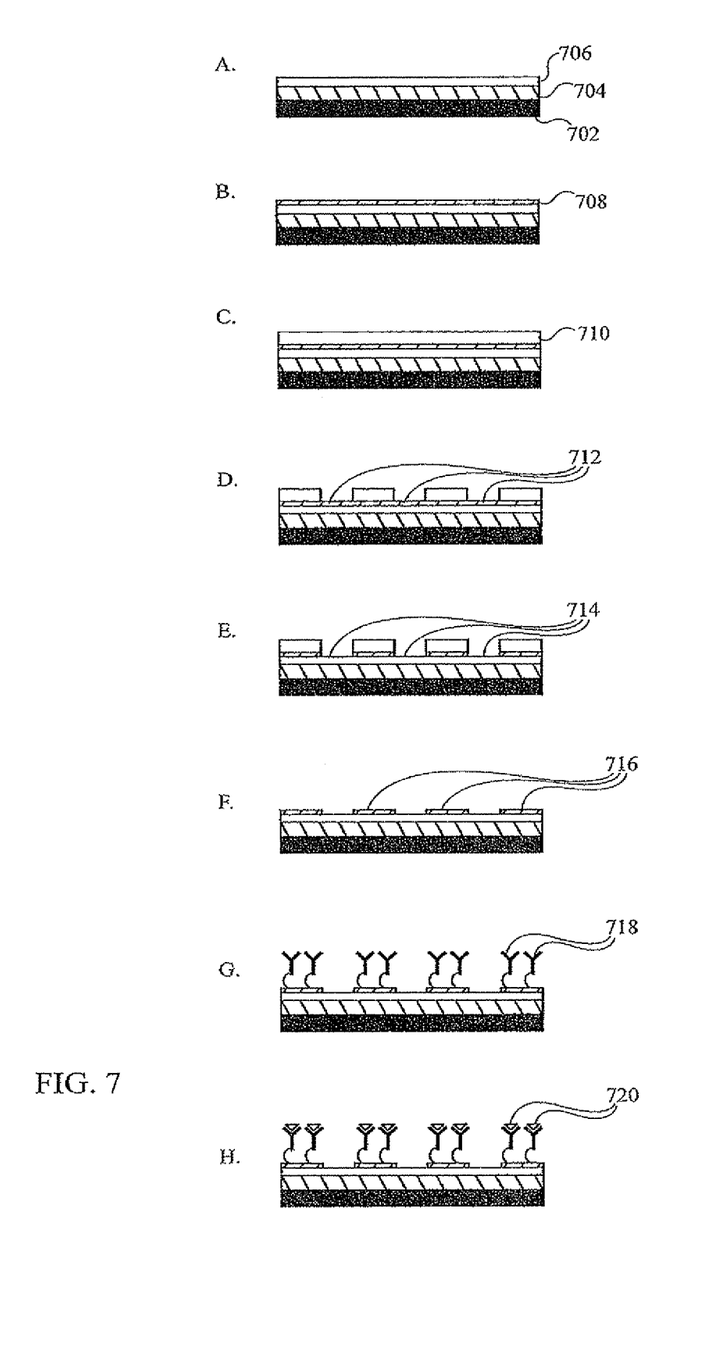
FIG. 7 shows a combined lithographic-biochemical functionalization scheme to achieve patterned immobilization of receptors.
Figure 8:
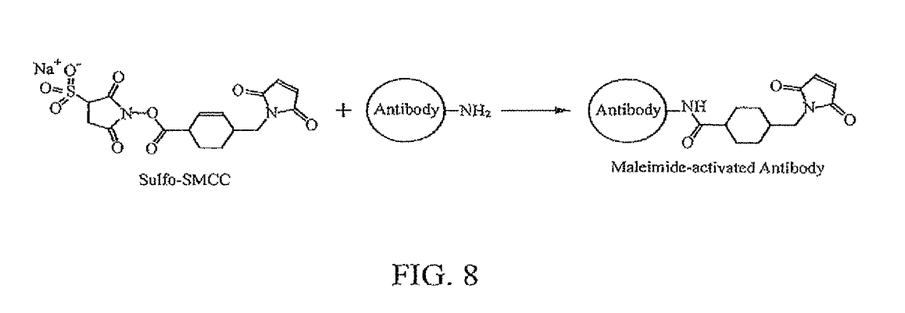
FIG. 8 shows an exemplary linker-antibody bonding of a commercial linker.
Figure 9:
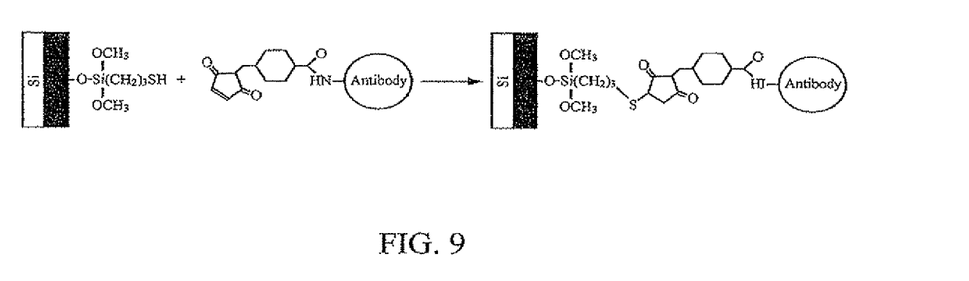
FIG. 9 shows the linkered antibody immobilization to a patterned silanized (glass or sol-gel) surface.

The functionalization is described with reference to FIGS. 7 to 9. Step A in FIG. 7 shows a sol-gel guiding layer 706 before silanization. Layer 706 is formed on top of a silica layer 704 on a silicon substrate 702. Step B shows the silanization step, in which the entire sol-gel surface was chemically (covalently) modified using Mercaptopropyltrimethoxysilane. The result was a molecular silane layer 708 with active groups of sulfhydryl, shown in FIG. 9. In step C, a photoresist layer 710 was spin coated on the silanized surface. In step D, the photoresist was patterned by photolithography. The purpose of this step was to form a photoresist mask that protects only the sensing branch regions, exposing other silane regions 712. In step E, unprotected silane regions 712 were exposed to Oxygen-Argon plasma. The reactive ions destroyed the silane functional groups in these regions leaving non-functional silanized areas 714. In step F, the remaining photoresist was removed using Acetone, exposing formerly protected silane regions 716 for antibody immobilization. In step G, linker-fused anti-Human CRP (GCRP-80A, ICL) antibodies 718 were covalently immobilized on these regions, thus completing the functionalization. Before the immobilization, the antibodies were activated by a bi-functional linker with a spacer branch of 8.3 Å which had a N-hydroxysuccinimide (NHS) ester at one end and maleimide groups on the other end. The NHS ester reacts with primary amines on the antibody molecule, at pH 7-9, to form bonds, FIG. 8, while maleimides on the other linker end react with sulfhydryl groups on the silanized surface, at pH 6.5-7.5, to form stable thioether bonds, FIG. 9. Step H shows the sensor surface with antibodies binding antigens 720 during the sensing process. The sensors underwent testing in a dry immunoassay, described next. More details of each step above may be found in Peled 2009, pages 148-150.

Dry Optical Based Immunoassay

Point-of-care applications normally require a single measurement of the concentration of specific substances in the sample liquid (e.g. blood or serum). Given the inherent disadvantages of wet optical based immunoassays (e.g. changes of the buffer index, which introduce errors in the measurement), this invention advantageously provides optical sensors that work in "dry" immunoassays. When the optical measurements are done with a dry sensor, there is no need of a complex flow system with a delicate and tight control of the flowing sample liquid temperature. However, since biology is inherently wet, in order to perform a dry optical measurement the ambient buffer needs to be removed post a biological step. This causes buffer salts to remain on the dry devices and may disrupt the sensor optical reading.

In the dry method developed herein, after the antibody immobilization, the surface of each sensor was thoroughly washed with a 0.1M ammonium bicarbonate buffer, in order to remove salts originating from the antibody solution and from the PBS buffer (pH 7.4, 0.5 liter, composition 450 ml deionized water, 50 ml PBS×10, 0.93 gr EDTA) used in the immobilization step. The drying procedure was based on lyophilization (cool-drying) using an ALPHA 1-5 Christ lyophilizer. This process causes the ammonium bicarbonate buffer and its volatile salts to evaporate completely under proper conditions, see Peled 2009, page 149. After the drying step, each sensor was calibrated by measuring its lasing spectrum. At this stage, the sensor was ready for the detection of CRP. The incubation with the analyte (CRP or BSA) was done in the ammonium bicarbonate buffer, after which the sensor was washed and dried again in the same lyophilization procedure (Peled 2009, page 150). Post drying, the sensor lasing spectrum was read again, providing the spectral shift (relative to the spectrum of control devices, see Peled 2009, pages 133-139) that represented the CRP or BSA detection readout.

Modeling Results

The effective (mean) thickness of the bound layer of a protein antigen such as CRP depends on many factors, including the surface density of the immobilized receptors, the analyte concentration in the sample liquid and the affinity of the analyte-receptor association. In the performed experiments, the effective thickness of the bound CRP dried layer was expected to fall within the range of 0.1-1 nm. The refractive index of dried proteins is about 1.45. A Matlab based program was used to calculate corresponding effective index changes ($n_{eff_{Ab}} - n_{eff_A}$). These were found to be about $10^{-5}$ to $10^{-4}$. The respective corresponding peak wavelength shift calculated for a 10 mm long binding waveguide branch (Sensor type #2) from equations 1 to 5 was 1.2 to 12 nm, respectively. In order to fairly cover this range and in order to be able to follow the peak shift and avoid misidentification of a specific peak after the spectral shift, three exemplary bio-binding section lengths (on sensing branches) were designed for each device: 1 mm, 2 mm and the full length of the sensing branch minus 400 µm, i.e. 2.6 mm in Sensor type #1, 9.6 mm in Sensor type #2 and 19.6 mm in Sensor type #3.

Experimental Results

Figure 10:
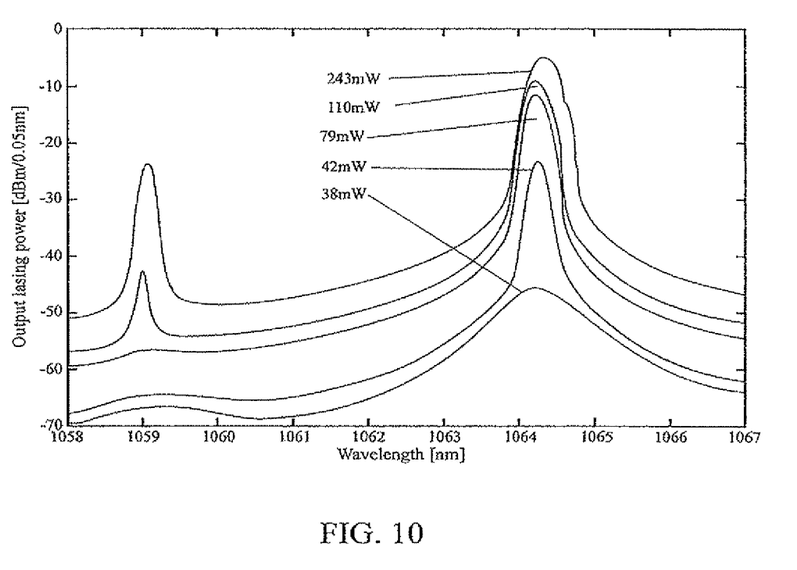
FIG. 10 shows the lasing spectrum evolution as function of pumping power in a light-emitting Y-branch ICI sensor of the invention.

Experimental ICI laser sensor spectra shapes as function of pump power are shown in FIG. 10. The figures shows the evolution of the lasing spectra as a function of input pump power as measured for an exemplary, Y-branch ICI laser with 3 mm and 3.06 mm long interfering branches and an overall length of 30 mm. The reflection grating period was 355 nm. At the higher pumping powers there are two sharp peaks separated by about 5 nm, matching closely peaks expected in the design of the device. Binding of a target to a functionalized branch causes a shift in these peaks due to the ICI effect.

Figure 11:
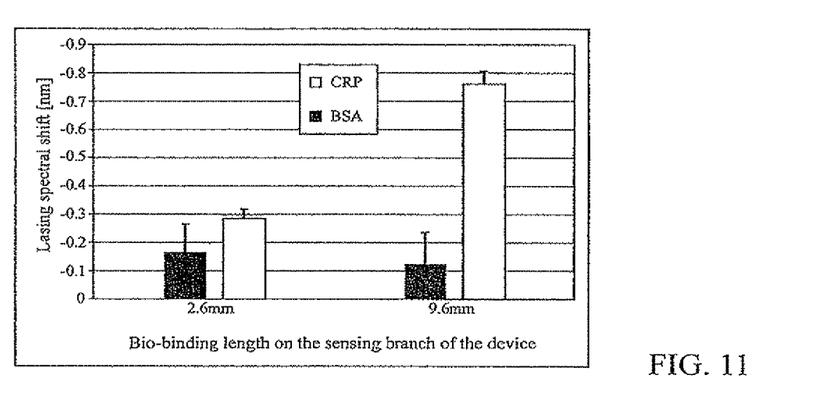
FIG. 11 shows experimental results of lasing spectra shifts post incubation with CRP and BSA for light-emitting ICI sensors with different lengths.

Spectral shifts due to incubation with both CRP and BSA were measured experimentally. Since the absolute values of spectral shifts as a result of CRP/BSA binding are very small relative to the figure scale (less than 1 nm), spectral shift experimental results are illustrated on a graph as in FIG. 11. FIG. 11 shows lasing spectra shifts post incubation with CRP and BSA for Sensors type #1 and type #2. As mentioned, the specific spectral shifts discussed herein are less than 1 nm, but well within the measurement capabilities of modern spectrometers. Most evident is the difference in the spectral shift of the devices with the 9.6 mm long bio-binding section (where the shift for CRP binding is −0.76 nm vs. a shift of −0.125 nm for BSA binding). That is, the spectral shift in devices exposed to CRP is six times larger than in devices exposed to BSA. In addition, while the spectral shift of devices exposed to CRP increased with the length of their bio-binding regions (−0.29 nm in the Sensor type #1 and −0.76 nm in Sensor type #2), as expected theoretically, this tendency did not show up in devices exposed to BSA. On the contrary, the shift due to incubation with BSA in the devices with longer bio-binding sections devices was smaller than in the devices with the shorter bio-binding sections (−0.125 nm vs. −0.171 nm). Finally, the deviation (dispersion) of the measured spectral shifts of the devices exposed to CRP was about 6%, which is extremely small in comparison to the 60% and 85% measured in devices exposed to BSA. This proves that the CRP measurements reflect specific binding, whereas the BSA measurements reflect nonspecific adsorption of BSA molecules. More details are provided in Peled 2009, pages 133-139.

Although the disclosure has been provided in the context of certain embodiments and examples, it will be appreciated by those of ordinary skill in the art that the disclosure extends beyond the specifically described embodiments to other alternative embodiments and/or uses and obvious modifications and equivalents thereof. Accordingly, the disclosure is not intended to be limited by the specific disclosures of embodiments herein. For example, the interferometric waveguide structures are not limited to Y-branch, MZI and AWG geometries. For example, the light-emitting sensor waveguide materials are not limited to sol-gels and the excitation of the light emitting material included in these waveguides is not limited to optical excitation (pumping). For example, ICI sensors of the invention may be formed in light emitting polymers or in semiconductors, where internal light generation is excited optically or electrically. In electrically pumped ICI sensors, an electrical pump power source may be integrated in the same chip with the sensor. For example, the target material is not limited to CRP, but may be any target material for which appropriate receptor and immobilization procedures are available or can be developed with reasonable effort. For example, the ICI sensor optical operation is not limited to "dry" immunoassays, but can be performed also in a liquid phase, e.g. via a flow cell provided with an optical window. For example, the input (in-coupling) and output (out-coupling) of light into/from the sensor is not limited to remote coupling through gratings, but may also be performed by other known coupling methods such as fiber butt-coupling.

Accordingly, the drawings and description disclosed herein illustrate technologies related to the invention, show examples of the invention, and provide examples of using the invention and are not to be construed as limiting the present invention. Known methods, techniques, or systems may be discussed without giving details, so to avoid obscuring the principles of the invention. As it will be appreciated by one of ordinary skill in the art, the present invention can be implemented, modified, or otherwise altered without departing from the principles and spirit of the present invention. Therefore, the scope of the present invention should be determined by the following claims and their legal equivalents.

All publications and patents mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A device for sensing an entity comprising an intra-cavity interferometric waveguide sensor which includes:
    an imbalanced Y-branch channel waveguide structure having:
        two unequal waveguide branches for interacting with the entity,
        an active medium capable of generating light emitted from the sensor, and
    wherein the emitted light undergoes a parameter change upon interaction of at least one of the waveguide branches with the entity.

2. The device of claim 1, wherein the parameter change is a spectral shift.

3. The device of claim 2, wherein the two waveguide branches have different widths.

4. The device of claim 1, wherein the two waveguide branches interact with the entity by having non-functionalized surfaces.

5. The device of claim 1, wherein the two waveguide branches interact with the entity by having one waveguide branch functionalized with a receptor which targets the entity and the other waveguide branch non-functionalized.

6. The device of claim 1, wherein the two waveguide branches interact with the entity by being both functionalized with a receptor which targets the entity.

7. The device of claim 6, wherein the receptor is of the same type but placed over a first sized region in one waveguide branch and over a second, different sized region in the other waveguide branch.

8. The device of claim 6, wherein the receptor is of a first type in one waveguide branch and of a second, different type in the other waveguide branch.

9. The device of claim 1, wherein the sensor is formed in a sol-gel material.

10. The device of claim 1, wherein the sensed entity is C Reactive Protein.

11. A method for sensing an entity comprising the steps of:
 a) providing an intra-cavity interferometric waveguide sensor which includes an imbalanced Y-branch channel waveguide structure having two unequal waveguide branches for interacting with the entity;
 b) emitting internally generated light from the Y-branch channel waveguide structure, the emitted light undergoing a parameter change upon interaction of at least one of the waveguide branches with the entity; and
 c) sensing an emitted light parameter change which is indicative of the interaction to sense the entity.

12. The method of claim 11, further comprising functionalizing one wavelength branch with an appropriate receptor that interacts with the entity.

13. The method of claim 12, wherein the step of sensing includes performing a dry measurement of a sensed entity value.

14. The method of claim 13, wherein the performing a dry measurement includes:
 i. obtaining an emitted light spectrum with a dry sensor before interaction with the sensed entity,
 ii. obtaining an emitted light spectrum with a dry sensor after interaction with the sensed entity, and
 iii. comparing the before and after interaction emitted light spectra, thereby obtaining a spectral shift indicative of the sensed entity value.

15. The method of claim 13, wherein the sense entity is selected from the group consisting of a biological entity and a chemical entity.

16. The method of claim 15, wherein the biological entity is C Reactive Protein.

17. A C Reactive Protein (CRP) sensor comprising:
 a) an intra-cavity interferometric (ICI) waveguide structure having two branches and including a light-emitting material which emits internally generated light; and
 b) a functionalized region on at least one branch and used for binding CRP, the CRP binding detectable by a parameter change in the emitted light.

18. The CRP sensor of claim 17, wherein the parameter change is a spectral shift.

19. The CRP sensor of claim 17, wherein the ICI waveguide structure is a Y-branch channel waveguide structure.

20. The CRP sensor of claim 19, wherein the Y-branch channel waveguide structure is imbalanced.

21. The CRP sensor of claim 17, wherein the ICI waveguide structure is a Mach Zehnder interferometer channel waveguide structure.

22. The CRP sensor of claim 17, wherein the emitted light is emitted as a laser beam.

23. The CRP sensor of claim 17, wherein the ICI waveguide structure includes a sol-gel layer.

24. The CRP sensor of claim 17, wherein the functionalized region is functionalized for dry CRP sensing.

* * * * *